United States Patent [19]

Howorth

[11] Patent Number: 4,531,956
[45] Date of Patent: Jul. 30, 1985

[54] STERILE AIR TROLLEY

[75] Inventor: Frederick H. Howorth, Farnworth, United Kingdom

[73] Assignee: Howorth Air Engineering Limited, Farnworth, England

[21] Appl. No.: 433,810

[22] Filed: Oct. 12, 1982

[30] Foreign Application Priority Data

Nov. 10, 1981 [GB] United Kingdom ................ 8133944

[51] Int. Cl.³ .......................................... B01D 46/12
[52] U.S. Cl. ..................................... 55/279; 55/276; 55/356; 55/410; 55/419; 55/472; 55/473; 55/482; 55/484; 55/DIG. 29; 98/36
[58] Field of Search ................ 55/276, 279, 356, 410, 55/419, 467, 471, 472, 473, 482, DIG. 29, DIG. 18, 484; 98/36, 40 C

[56] References Cited

U.S. PATENT DOCUMENTS

| 1,505,914 | 8/1924 | Witteborg | 98/36 |
| 2,347,334 | 4/1944 | Schmieg | 55/DIG. 18 X |
| 3,021,776 | 2/1962 | Kennedy | 55/DIG. 29 X |
| 3,251,177 | 5/1966 | Baker | 55/472 X |
| 3,279,883 | 10/1966 | Thompson et al. | 98/36 X |
| 3,426,512 | 2/1969 | Nesher | 55/467 X |
| 3,537,381 | 11/1970 | Austin | 55/DIG. 18 X |
| 3,614,860 | 10/1971 | Grellsson | 55/276 |
| 3,776,121 | 12/1973 | Truhan | 55/DIG. 29 X |
| 3,838,556 | 10/1974 | Finger | 55/472 X |
| 3,935,803 | 2/1976 | Bush | 55/473 X |
| 4,038,974 | 8/1977 | Pielkenrood | 98/36 X |

FOREIGN PATENT DOCUMENTS 2403136 8/1974 Fed. Rep. of Germany ......... 98/36

Primary Examiner—Kathleen J. Prunner
Attorney, Agent, or Firm—Ross, Ross & Flavin

[57] ABSTRACT

A sterile air trolley introduces sterile air into a zone adjacent all outermost boundaries of an upper part of a casing which extends laterally outboard of all sides of a lower part of a casing. The sterile air so introduced is without or free of any contaminated ambient air being entrained by the air so being emitted from the trolley and so introduced into the zone.

5 Claims, 3 Drawing Figures

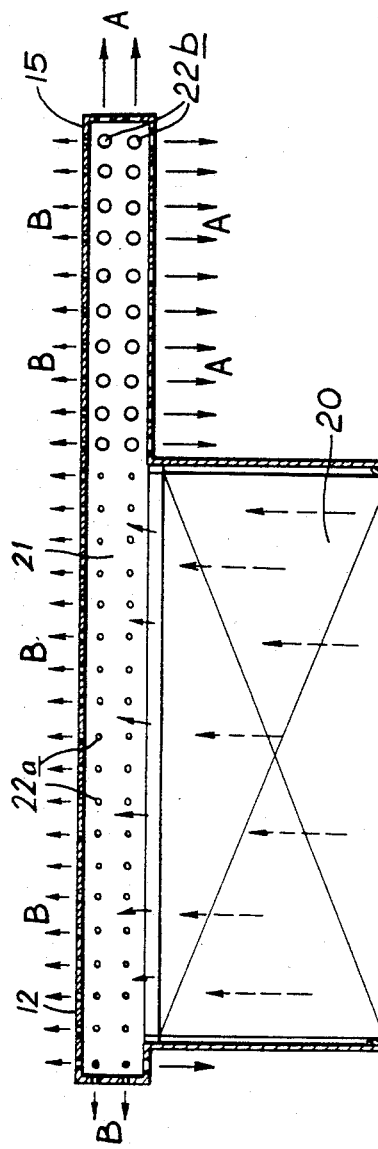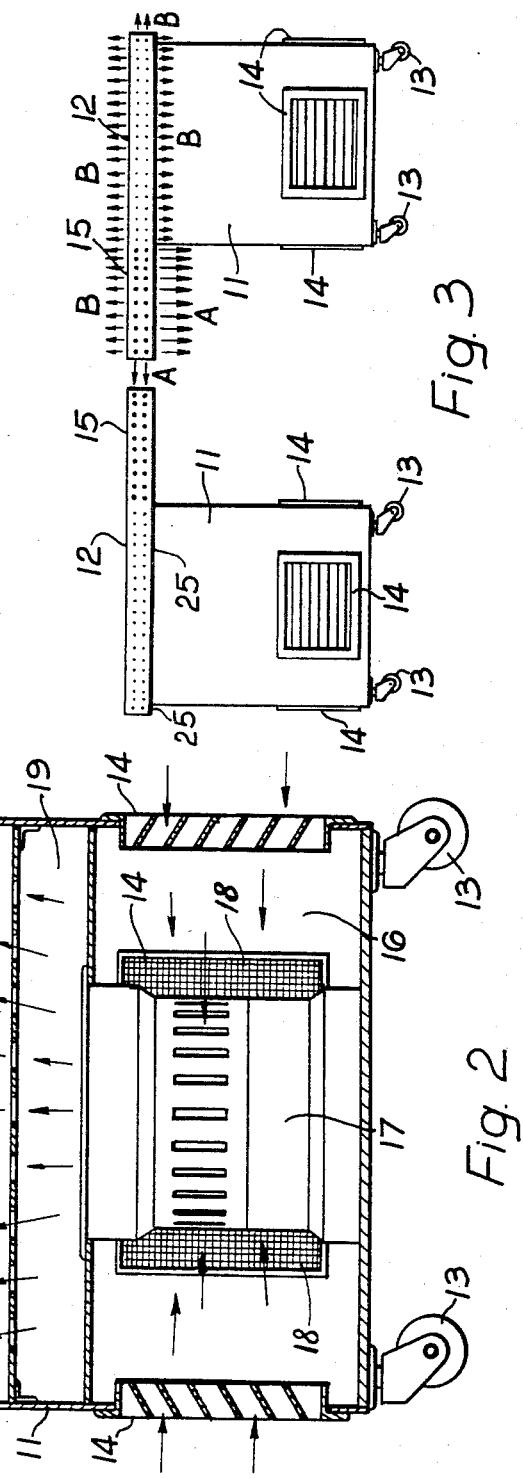
Fig. 2
Fig. 3

STERILE AIR TROLLEY

FIELD OF INVENTION

This invention relates to a sterile air trolley, particularly for provision of a sterile air zone for surgery and surgical instruments.

BACKGROUND ART

Air in an operating theatre is a vehicle for bacterial and gaseous contaminants either generated within the theatre or brought in from outside by movement of people and air. Since many of these airborne contaminants are harmful to patients or to those who work in the operating theatre, it will be appreciated that their removal is necessary on medical as well as financial grounds. In general, removal of such airborne contaminants as bacteria-carrying particles and anaesthetic gases exhaled by the patient is accomplished by specialised air-conditioning systems currently installed in many operating theatres.

An object of the present invention, is the provision of a bacteria-free zone in the theatre where sterile items, particularly surgical instruments may be safely removed from their protective wrappings and in which surgery may be performed without any risk of airborne bacterial contamination.

DISCLOSURE OF INVENTION

With this object in view, the present invention provides a sterile air trolley comprising a mobile casing having one or more air inlets in its lower region and a plurality of air outlets in its upper region and enclosing impeller means operative to move air in through said inlet or inlets, through filter means and out of the casing by way of the outlets.

The impeller means preferably comprises a motor-driven fan.

The filter means is preferably located above the impeller means, but it may alternatively or additionally be located across each of the inlets.

The upper region of the casing may extend laterally beyond one or more sides of the lower region of the casing.

The air outlets are conveniently in the form of a plurality of substantially circular apertures in the upper region of the casing. The size of these apertures may vary from one part of the casing to another so that resultant air outflow from the trolley may be graded, small diameter apertures allowing only a low rate of air flow and larger diameter apertures allowing a correspondingly greater rate of air flow so that areas adjacent these larger apertures are rendered substantially entirely free of airborne contaminants when the impeller means inside the trolley casing is switched on.

The invention will be described further, by way of example, with reference to the accompanying drawings in which:

BRIEF DESCRIPTION OF DRAWINGS

FIG. 2 is a cross-section of the trolley along the line 2—2 of FIG. 1; and

FIG. 3 is a side elevation to a smaller scale of two of the trolleys illustrated in FIGS. 1 and 2 as arranged for use adjacent an operating table.

DETAILED DESCRIPTION OF INVENTION

Figure 1:
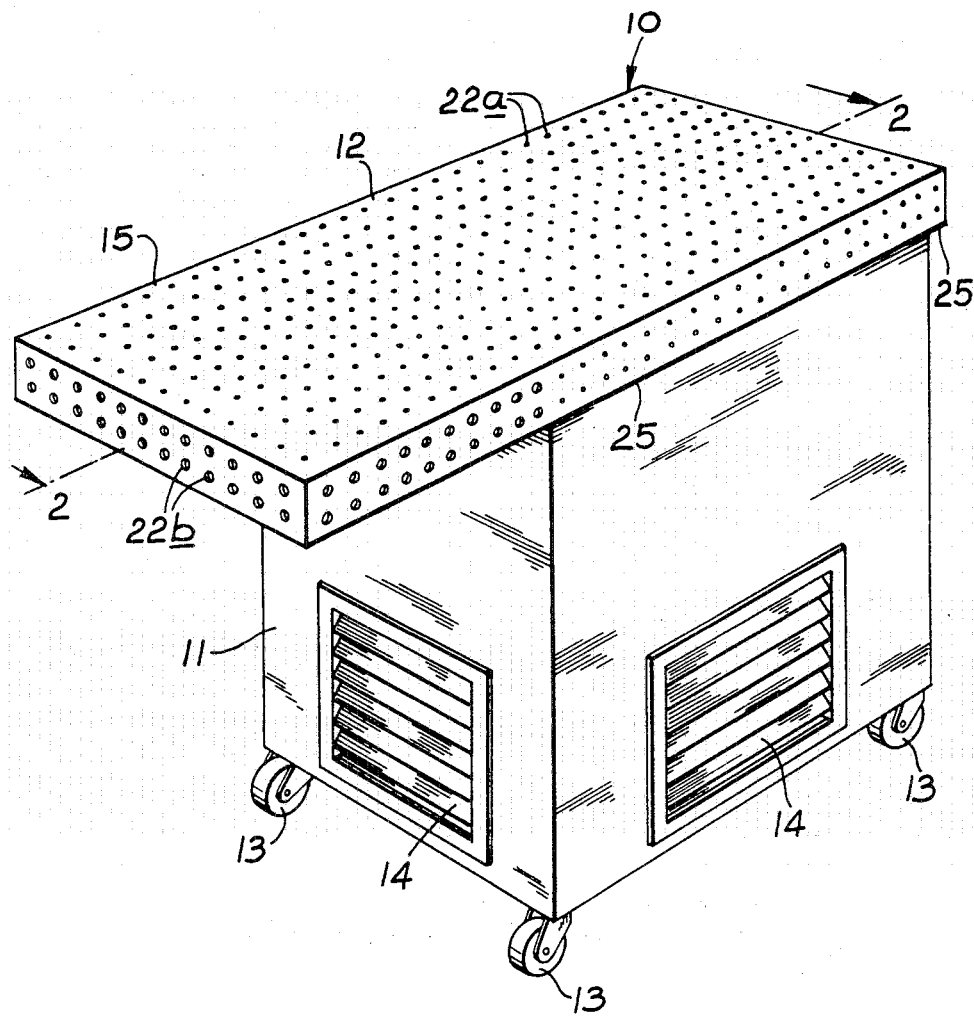
FIG. 1 is a perspective view of a preferred embodiment of the sterile air trolley of the present invention.

As shown in FIG. 1, a sterile air trolley comprises a box-like casing 10 having a lower region or base 11 and an upper region 12. Four castors 13 are attached to the underside of lower region 11, one castor at each of the four corners thereof. Four substantially rectangular louvred air inlets 14 are respectively located adjacent the lower edge of each of the four side walls of the lower region 11. The upper region 12 of the casing 10 extends laterally beyond all four sides of the lower region 11 to form, at one side, a limb 15 and at the other three sides an overhang 25 of about three centimeters.

The internal structure of the trolley is shown in FIG. 2. The lower region or base 11 of the casing 10 encloses three chambers disposed vertically one on top of the other. The lower end of the base 11 encloses a suction chamber 16 at the centre of which is located impeller means in the form of a motor-driven fan, generally indicated at 17. One inlet 14 is disposed in each of the four walls of the suction chamber 16. Prefilters 18 are firmly attached at the inner side of each of the inlets 14. Immediately above the fan suction chamber 16 is a plenum chamber 19 and above that, still within the lower region or base 11 of the trolley casing 10, is a chamber 20, wherein a silencer and a HEPA (high efficiency particulate air) filter are located.

The upper region 12 of the casing 10, including the limb 15 and the overhang 25, encloses a diffusion chamber 21 having a plurality of air outlets in the form of substantially circular apertures 22a, 22b in the casing 10. These circular apertures 22a, 22b are regularly arranged equidistant from one another and in a series of parallel rows. In this particular embodiment there are two rows of apertures 22a, 22b in the side and end walls of the diffusion chamber 21 and one row of apertures 22a in the underside of overhang 25. As indicated, the apertures 22b in the side walls, end wall and undersurface of the limb 15 are of larger diameter than the apertures 22a in the remainder of the upper region 12 of the casing 10.

When the above described sterile air trolley is to be used to create a sterile air zone adjacent the outer surface of the upper region 12 of the casing 10, the fan 17 of the trolley is actuated. Air is drawn into the suction chamber 16 through the prefilters 18 of the inlets 14, as indicated in FIG. 2. From the suction chamber 16, the air is drawn into the fan 17 itself and thence is driven upward into the plenum chamber 19 and through the silencer and HEPA filter into the diffusion chamber 21. Airflow outwards from the diffusion chamber 21, is of course, by way of the apertures 22a, 22b. There is a higher rate of airflow A from the larger diameter apertures 22b in the end wall, side walls and lower surface of the limb 15 compared to the airflow B from the smaller diameter apertures 22a in the remainder of the upper portion 12 of the casing 10. Areas adjacent the high airflow outlets 22b have a greater probability of being completely free of contaminants than areas adjacent the lower airflow outlets 22a. The low airflow outlets 22a in the sides and undersurface of overhang 25 are of particular importance in that the air issuing therefrom (as shown for one trolley in FIG. 3) prevents an upflow of contaminated air adjacent the trolley sides.

When a sterile air zone is required during a surgical operation, it is envisaged that either one or two trolleys of the aforementioned type will be moved into position at the side or end of an operating table. In the event of two trolleys being used at either side, their respective limbs 15 may project towards each other as shown in FIG. 3, and are disposed adjacent the operating site of any patient lying on the table. Once the fans of the respective trolleys are switched on and sterile air zones are being created as described above, the sterilized surgical instruments may safely be removed from their wrappings and deposited on the horizontal upper surface of the upper regions 12 of the respective trolley casings 10. The low airflow B from the small apertures 22a in the aforesaid upper surface is insufficient to blow away any sterile wrappings which are still required. Also the surfaces may be covered with an air permeable sterile drape before the instruments are deposited thereon. Sterile air A issuing at a higher rate from apertures 22b is diffused over the operating site from the end walls, side walls and undersurfaces of the two limbs 15.

In a similar manner the limbs 15 of one or more trolleys may be positioned over a bed when wounds are being dressed.

The above described embodiment is, of course, illustrative and not limitative of the scope of the invention and variations are possible. The dimensions of the trolley and its component parts may differ from those described. In particular, the upper perforate region of the casing may extend laterally beyond only one, two or three sides of the lower region or base so that the diffusion chamber is of any desired shape or size. The apertures may vary in shape, being, for example round, rectangular or oval. Also the arrangement of the apertures and distribution of larger and smaller apertures may vary as required by the intended use of the trolley.

I claim:

1. A sterile air trolley comprising:
   a box-like casing having a four-sided lower region and an upper region extending laterally beyond all four sides of the lower region in forming a limb at one of the sides and an overhang at each of the other three sides,
   an air inlet through each of the four sides of the lower region,
   the upper region enclosing a diffusion chamber defined by an upper surface and sides and the undersides of the overhangs and of the limb,
   a plurality of air outlets in the upper surface, the sides and the undersides of the overhangs and the limb of the diffusion chamber,
   impeller means within the lower region,
   a filter disposed across each air inlet,
   the impeller means being operative to draw air into the lower region of the casing through the air inlets and filters and out of the casing by way of the air outlets of the upper region resulting in substantially vertical air flow from the upper surface and undersides and lateral air flow from the upper region sides to provide an effective sterile air zone in the immediate vicinity of the upper region, and
   casters attached to the underside of the lower region.

2. The trolley as set forth in claim 1 wherein the impeller means comprises a motor driven fan.

3. The trolley as set forth in claim 1 including secondary filter means arranged within the casing above the impeller means and below the air outlets of the upper region.

4. The trolley as set forth in claim 1 wherein the air outlets are in the form of substantially circular apertures.

5. The trolley as set forth in claim 1 wherein the air outlets vary in size from one part of the upper region to another part of the upper region for the grading of air flow from the trolley.

* * * * *